(12) United States Patent
Itoi et al.

(10) Patent No.: US 12,042,407 B2
(45) Date of Patent: Jul. 23, 2024

(54) SOLE OF ATHLETIC PROSTHETIC LEG

(71) Applicant: BRIDGESTONE CORPORATION, Tokyo (JP)

(72) Inventors: Dyta Itoi, Tokyo (JP); Kohei Sahashi, Tokyo (JP)

(73) Assignee: BRIDGESTONE CORPORATION, Tokyo (JP)

( * ) Notice: Subject to any disclaimer, the term of this patent is extended or adjusted under 35 U.S.C. 154(b) by 3 days.

(21) Appl. No.: 17/048,095

(22) PCT Filed: Apr. 17, 2019

(86) PCT No.: PCT/JP2019/016543
§ 371 (c)(1),
(2) Date: Oct. 16, 2020

(87) PCT Pub. No.: WO2019/203286
PCT Pub. Date: Oct. 24, 2019

(65) Prior Publication Data
US 2021/0161683 A1 Jun. 3, 2021

(30) Foreign Application Priority Data

Apr. 17, 2018 (JP) ................. 2018-079458
Jul. 24, 2018 (JP) ................. 2018-138810

(51) Int. Cl.
*A61F 2/66* (2006.01)
*A61F 2/50* (2006.01)

(52) U.S. Cl.
CPC ........ *A61F 2/66* (2013.01); *A61F 2002/5079* (2013.01); *A61F 2002/665* (2013.01)

(58) Field of Classification Search
CPC ..... A61F 2/66; A61F 2002/5079; A43B 3/108
See application file for complete search history.

(56) References Cited

U.S. PATENT DOCUMENTS

| 2,408,214 | A | | 9/1946 | Husted | |
|---|---|---|---|---|---|
| D426,947 | S | * | 6/2000 | Pollastrelli | ............ D2/947 |

(Continued)

FOREIGN PATENT DOCUMENTS

| EP | 0766932 A1 | 4/1997 |
|---|---|---|
| JP | 2016150189 A | 8/2016 |

(Continued)

OTHER PUBLICATIONS

Jul. 23, 2019, International Search Report issued in the International Patent Application No. PCT/JP2019/016543.

(Continued)

*Primary Examiner* — Christie Bahena
(74) *Attorney, Agent, or Firm* — KENJA IP LAW PC

(57) ABSTRACT

In a sole which is attached to a ground contact region of an athletic prosthetic leg which has a leaf-spring-like leg portion extending to a side of a toe via at least one curved portion, the ground contact region extending from the toe to a side of the curved portion in an arc, the sole includes a bottom surface having a shape conforming to an extending shape of the ground contact region, and, in the bottom surface, a region at the side of the curved portion, which is defined by a border as a line extending in a width direction of the leg portion through a contact point with a road surface in a standing state of a wearer who wears the athletic prosthetic leg, has a higher drainage performance compared with a region other than the region at the side of the curved portion.

11 Claims, 15 Drawing Sheets

(56) References Cited

U.S. PATENT DOCUMENTS

| | | | |
|---|---|---|---|
| 8,535,390 B1* | 9/2013 | Lecomte | A61F 2/78 623/53 |
| D895,245 S * | 9/2020 | Hardigan | D2/947 |
| 2007/0227038 A1* | 10/2007 | Edington | A43B 23/042 36/10 |
| 2007/0277038 A1* | 11/2007 | Hardy | H04L 9/0897 713/176 |
| 2009/0293314 A1* | 12/2009 | Dekovic | A43B 13/14 36/103 |
| 2015/0052781 A1* | 2/2015 | Hatfield | A43B 13/141 36/25 R |
| 2016/0045337 A1 | 2/2016 | Mackiewicz et al. | |
| 2017/0049585 A1 | 2/2017 | Boiten et al. | |
| 2017/0281371 A1 | 10/2017 | Green et al. | |
| 2017/0281372 A1 | 10/2017 | Rubie et al. | |

FOREIGN PATENT DOCUMENTS

| | | | | |
|---|---|---|---|---|
| WO | 2011064799 A1 | 6/2011 | | |
| WO | WO-2013049852 A2 * | 4/2013 | | A61F 2/60 |
| WO | 2017173200 A1 | 10/2017 | | |

OTHER PUBLICATIONS

Oct. 20, 2020, International Preliminary Report on Patentability issued in the International Patent Application No. PCT/JP2019/016543.

Jan. 7, 2022, search result of the Extended European Search Report issued by the European Patent Office in the corresponding European Patent Application No. 19787984.4.

Jan. 31, 2023, search result of Office Action issued by the China National Intellectual Property Administration in the corresponding Chinese Patent Application No. 201980026449.6.

Bridgestone's "Rubber Sole for Sports Prostheses" Pursuing the Grip and Durability Required by Paratriathlete Yukako Hata, car.watch.impress.co.jp, retrieved on Dec. 14, 2022, from URL: https://car.watch.impress.co.jp/docs/news/1117911.html.

Sep. 13, 2023, search result of Office Action issued by the China National Intellectual Property Administration in the corresponding Chinese Patent Application No. 201980026449.6.

pocket-lint.com, Retrieved on Oct. 23, 2023, from URL: https://www.pocket-lint.com/gadgets/news/nike/115074-sarah-reinstern-talks-nike-sole/, XP093067699.

* cited by examiner

SOLE OF ATHLETIC PROSTHETIC LEG

TECHNICAL FIELD

The present disclosure relates to a sole attached to a ground contact region of an athletic prosthetic leg, in particular, to a sole of an athletic prosthetic leg which inhibits slip of the prosthetic leg during a competition.

BACKGROUND

Conventionally, a prosthetic leg for a competition (hereinafter, referred to as an athletic prosthetic leg or simply referred to as a prosthetic leg) having a leaf-spring-like leg portion which extends via a curved portion to a side of a toe and in which a ground contact region extends from the toe to a side of the curved portion in an arc has been well-known. To such an athletic prosthetic leg having the leaf-spring-like leg portion, generally, a sole which abuts a road surface is attached to a bottom surface of the ground contact region.

For example, Patent Literature 1 illustrates a sole which is attached to a lower surface of a curved leaf-spring-like athletic prosthetic leg to correspond to sporting events such as jogging or running. In other words, Patent Literature 1 discloses a sole to which a spike is attached at a lower surface of the sole contacting a road surface or a sole provided with a number of outsole portions each having a hexagonal contact patch.

CITATION LIST

Patent Literature

PTL 1: Japanese Patent Laid-Open No. 2016-150189

SUMMARY

Technical Problem

However, in the sole illustrated in Patent Literature 1, inhibiting slip of the prosthetic leg, that is, anti-slip property is not at all considered. For example, running on a wet road surface is required in a case of a competition in rainfall etc. At that time, when a water film exists on the road surface, the water film is interposed between a bottom surface of the sole and the road surface while hindering ground contact of the bottom surface, resulting that slip is caused. Especially, on a road with a low coefficient friction u such as asphalt and a stone pavement, there has been a case where a wearer of the prosthetic leg hesitates further acceleration. Accordingly, a sole having a high anti-slip property has been required for the wearer of the prosthetic leg to satisfactorily exert his running skill as athletes.

An object of the present disclosure is to provide a sole of an athletic prosthetic leg having a high anti-slip property.

Solution to Problem

The inventor earnestly studied means to solve the problem. In other words, while a ground contact form of an athletic prosthetic leg has been reviewed in detail, the inventor newly found that the athletic prosthetic leg illustrates a unique ground contact form caused by the shape of a leaf-spring-like leg portion. Further, the inventor found that a high anti-slip property can be achieved by allowing a bottom surface of a sole to correspond to a ground contact form which is unique to the athletic prosthetic leg to separate functions of the sole, and completed the present disclosure.

According to the present disclosure, there is provided a sole of an athletic prosthetic leg, the athletic prosthetic leg having a leaf-spring-like leg portion extending to a side of a toe via at least one curved portion, the sole being configured to be attached to a ground contact region of the athletic prosthetic leg, the ground contact region extending from the toe to a side of the curved portion in an arc, wherein the sole includes a bottom surface having a shape conforming to an extending shape of the ground contact region, and, in the bottom surface, a region at the side of the curved portion has a higher drainage performance compared with a region other than the region at the side of the curved portion, the region at the side of the curved portion being defined by a border as a line extending in a width direction of the leg portion through a contact point with a road surface in a standing state of a wearer who wears the athletic prosthetic leg.

Advantageous Effect

Due to the present disclosure, a sole of an athletic prosthetic leg having a high anti-slip property can be provided. Attachment of this sole to the athletic prosthetic leg provides an effect of fully exerting an athlete's skill.

DETAILED DESCRIPTION

Hereinafter, with reference to the drawings, a sole of an athletic prosthetic leg of the present disclosure (hereinafter, it is also referred to as a sole) will be explained in detail with illustration of embodiments thereof.

Figure 1:
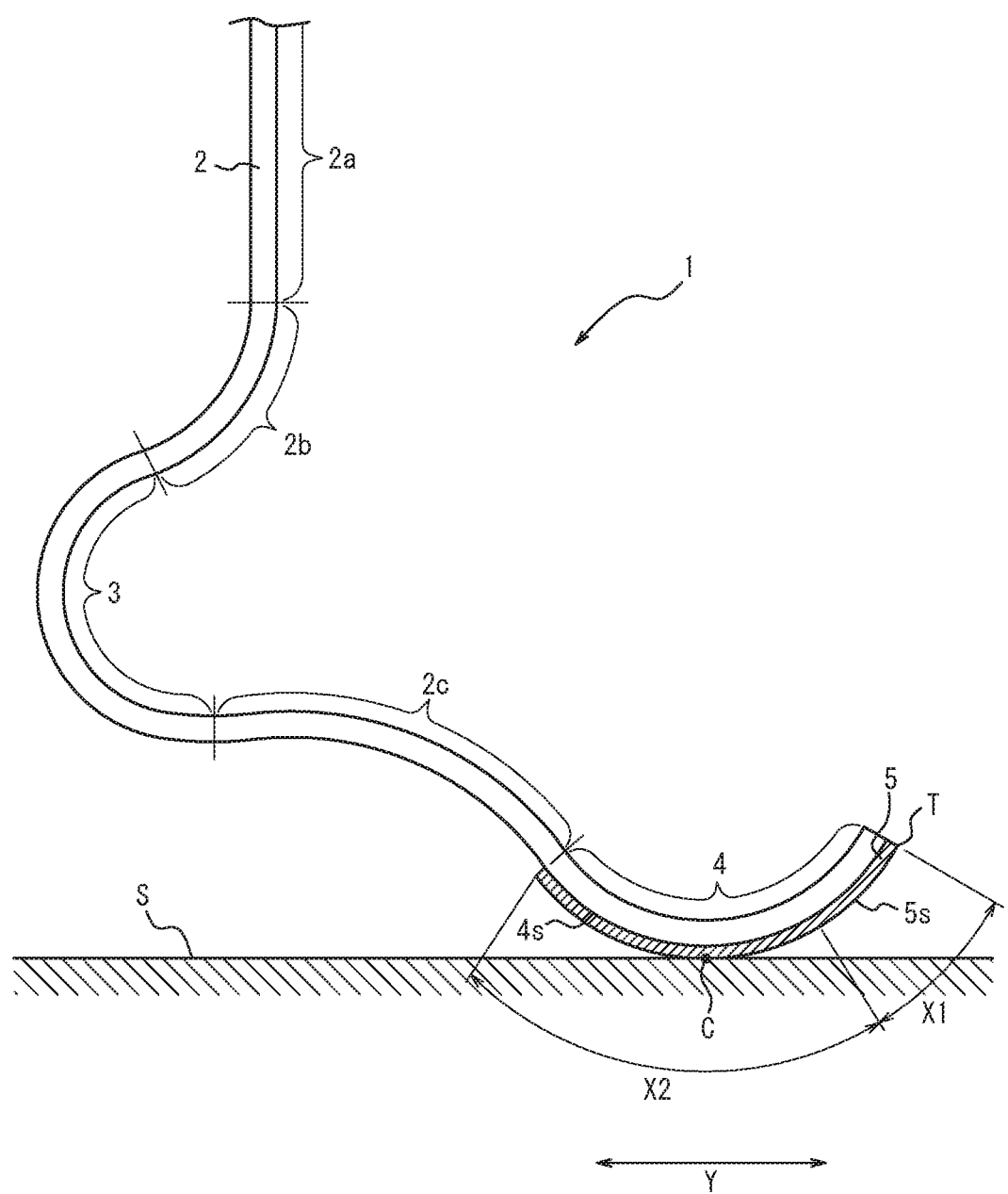
FIG. 1 is a side view of an athletic prosthetic leg to which a sole according to a first embodiment of the present disclosure is attached.

FIG. 1 is a side view of an athletic prosthetic leg 1 to which a sole 5 according to a first embodiment of the present disclosure is attached. The athletic prosthetic leg 1 has a leaf-spring-like leg portion 2, and the sole 5 is attached to a ground contact region at its tip side. Additionally, while illustration is omitted, a base end portion of the leg portion 2 is connected to a socket via an adapter and the socket houses a stump of a wearer's leg, whereby the wearer can wear the prosthetic leg. The adapter and the socket which correspond to the position of the stump of the leg, such as an above-knee prosthesis and a below-knee prosthesis, are used. FIG. 1 illustrates the leg portion 2 and the sole 5 in a standing state of the wearer who wears the athletic prosthetic leg 1.

Hereinafter, in this embodiment, in a height direction of the athletic prosthetic leg, a side where the leg portion 2 is connected to the adapter is referred to as a connection side, and a side where the leg portion 2 contacts a road surface S is referred to as a ground contact side. Also, a toe T of the athletic prosthetic leg 1 refers to a point at the forefront as a termination of the leg portion 2 extending from the connection side. Further, a direction extending from the toe T in parallel with the road surface S is referred to as a leg portion front-rear direction Y. Further, a widthwise direction of the leg portion 2 is referred to as a width direction W.

In this embodiment, the leg portion 2 of the athletic prosthetic leg 1 has a plate-like extending shape to the side of the toe T via at least one curved portion, in the illustrated example, one curved portion 3. In FIG. 1, the leg portion 2 is constituted by, in the order from the connecting side to the ground contact side, a straight portion 2a, a curved portion 2b which is convex to the side of the toe T, the curved portion 3 which is convex to a rear side in the leg portion front-rear direction Y, a curved portion 2c which is concave to the ground contact side and a ground contact portion 4 which is convex to the ground contact side to extend to the side of the toe T in an arc.

Additionally, although the material of the leg portion 2 is not limited, from a viewpoint of strength and weight saving, fiber reinforced plastic etc. is preferably used.

The ground contact portion 4 includes a ground contact region 4s extending from the toe T to the side of the curved portion 3 in an arc at the ground contact side, and the sole 5 is attached to the ground contact region 4s. The ground contact region 4s refers to the entire region abutting the road surface S when the wearer who wears the athletic prosthetic leg 1 executes straight running movement, and in a state that sole 5 is attached, the ground contact region 4s abuts the road surface S via the sole 5.

The sole 5 has a shape conforming to an extending shape of the ground contact region 4s. Also, the ground contact side of the sole 5 is a bottom surface 5s. As illustrated in FIG. 1, the bottom surface 5s has a shape in which an arc X1 and an arc X2 are continued from the toe T side to the curved portion 3 side. While the arc X1 and the arc X2 have a different radius of curvature to each other in this embodiment, they may include the same radius of curvature.

Also, the bottom surface 5s has different properties at one side and the other side, which are defined by a border as a line extending in the width direction W through a point C as a contact point with the road surface S in a standing state of the wearer when the athletic prosthetic leg 1 is worn. The point C is a point which firstly contacts the road surface S in arriving at standing. In other words, the standing state refers to a state that the wearer firstly contacts the road surface S by lowering the athletic prosthetic leg 1 to the road surface S from a state that the wearer supports his body by a healthy leg wearing no prosthetic leg when a prosthetic leg is used for only one leg, or the wearer supports his body by one prosthetic leg when prosthetic legs are used for both legs. Additionally, the point C is determined depending on the shape or an attachment aspect etc. of the prosthetic leg. In other words, the inventor newly conceived that the border for separating functions of the bottom surface 5s from a finding related to a ground contact form obtained from an experiment which will be described later uses the point C which is the contact point with the road surface S in the wearer's standing state as a standard.

An experiment result of the ground contact form of the bottom surface 5s as described above will be explained below using FIGS. 2A, 2B, 2C and 2D. FIGS. 2A, 2B, 2C and 2D are drawings for explaining in stages movement of the leg portion 2 and the ground contact form of the bottom surface 5s when the wearer who wears the athletic prosthetic leg 1 having the above configuration executes straight running. In each drawing, an upper portion is a side view of the leg portion 2 and the sole 5, and a lower portion illustrates a transition of the ground contact form of the bottom surface 5s when the wearer who wears the athletic prosthetic leg 1 executes straight running.

Figure 2A:
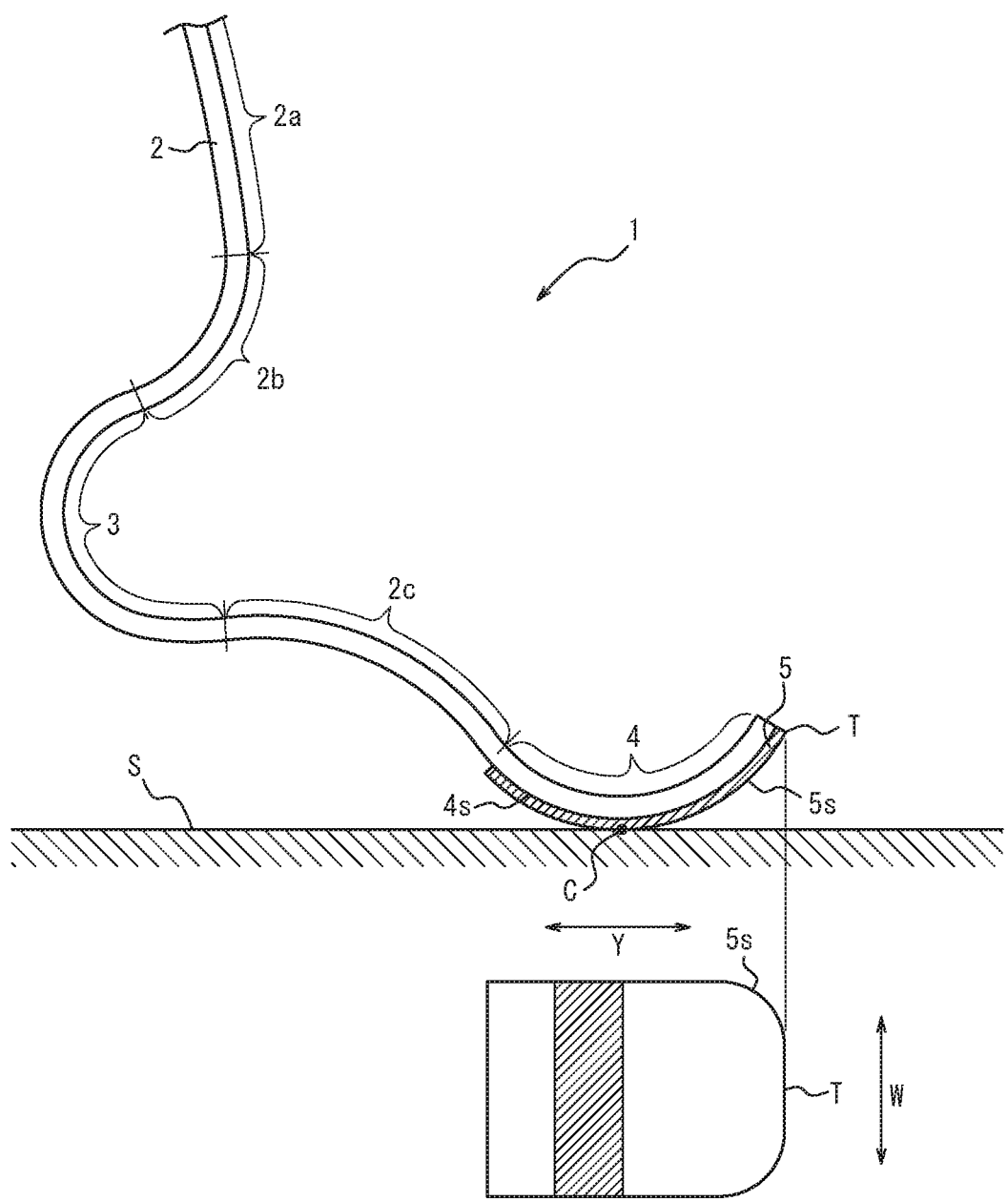
FIG. 2A is a drawing for explaining in stages movement of a leg portion and a ground contact form in a case where the athletic prosthetic leg is worn and a wearer executes straight running.

In other words, FIG. 2A illustrates a state that the wearer lowers the raised athletic prosthetic leg 1 to the road surface S and the entire weight is loaded on the athletic prosthetic leg 1. As illustrated in the lower portion of the drawing, in the bottom surface 5s, a region at the side of the curved portion 3 from the point C contacts the ground.

Figure 2B:
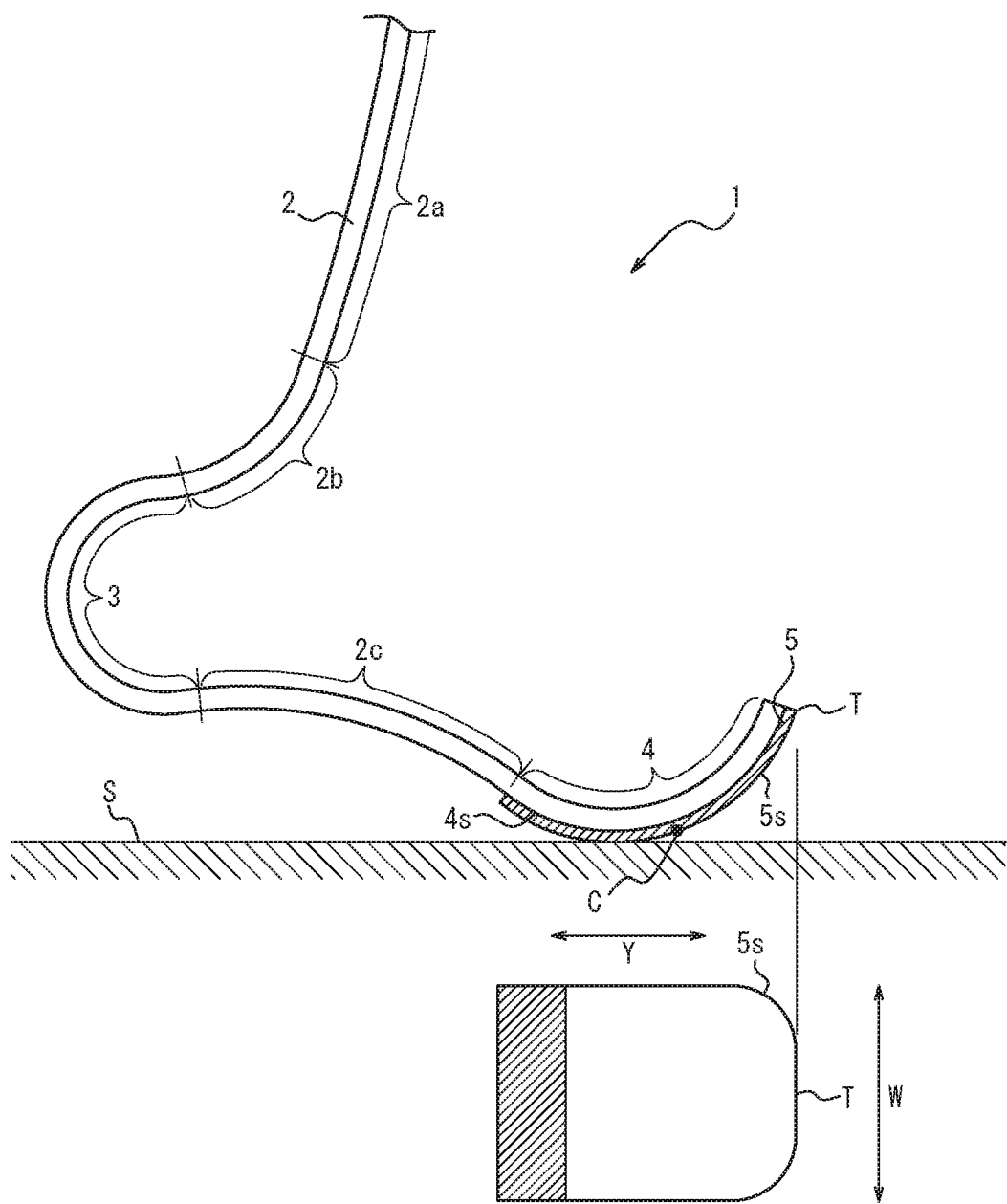
FIG. 2B is a drawing for explaining in stages the movement of the leg portion and the ground contact form in a case where the athletic prosthetic leg is worn and the wearer executes straight running.

FIG. 2B illustrates a state that the wearer steps forward, from the state of FIG. 2A, while the entire weight remains to be loaded on the athletic prosthetic leg 1. In a case of running of a healthy person, such a step form is generally applied that ground contact is sequentially executed from a heel side toward a toe side of a shoe sole which firstly contacts to the ground, while in the athletic prosthetic leg 1, the ground contact region is moved to 5 the side of the curved portion 3 from a portion which firstly contacts the ground.

Figure 2C:
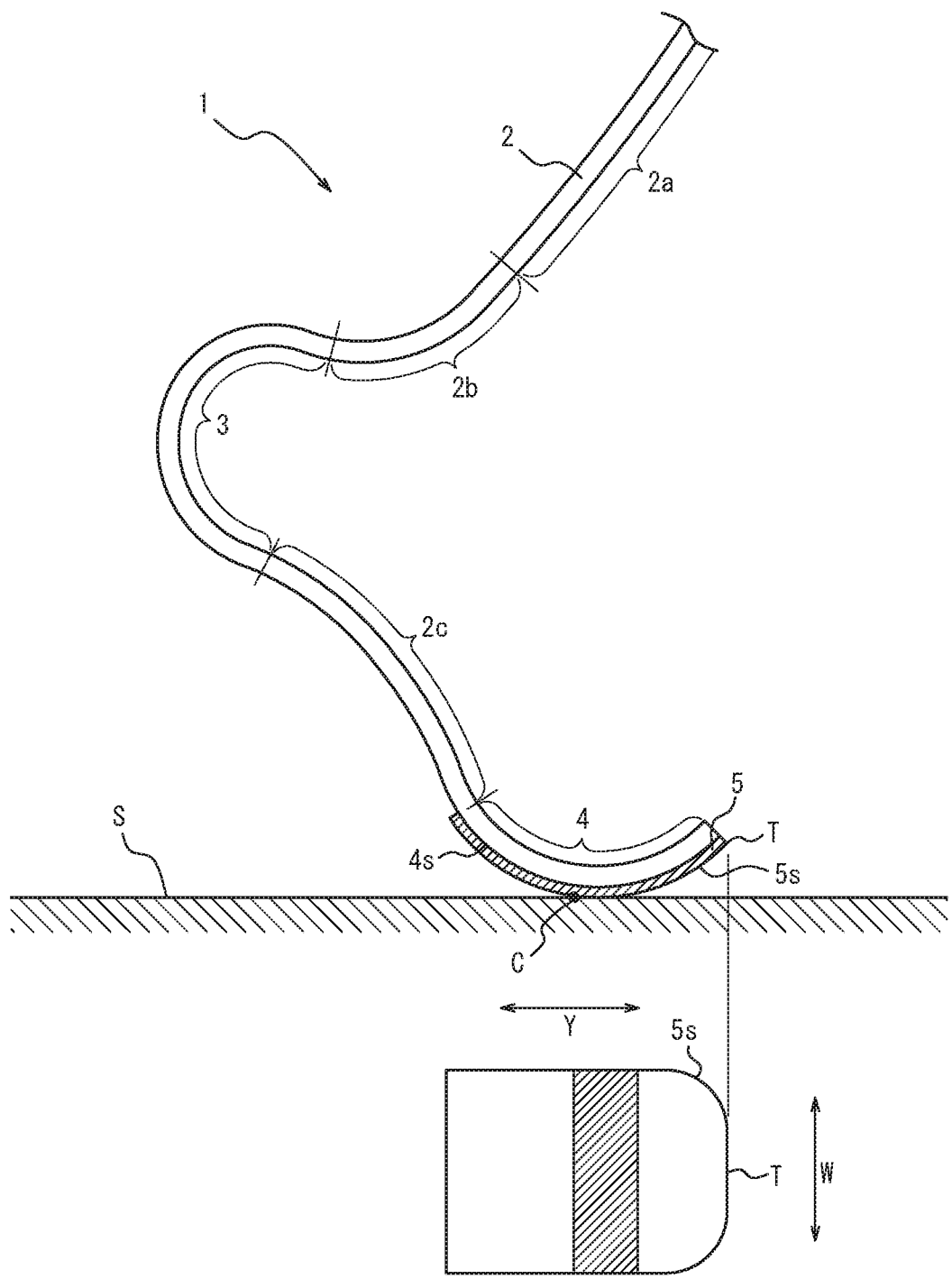
FIG. 2C is a drawing for explaining in stages the movement of the leg portion and the ground contact form in a case where the athletic prosthetic leg is worn and the wearer executes straight running.

FIG. 2C illustrates a state that the wearer starts a kick-out movement of the athletic prosthetic leg 1 by shaking an opposite leg from the leg 10) wearing the athletic prosthetic leg 1 forward. Entering into this kick-out movement, the athletic prosthetic leg 1 contacts the ground at a region at the side of the toe T from the point C of the bottom surface 5s.

Figure 2D:
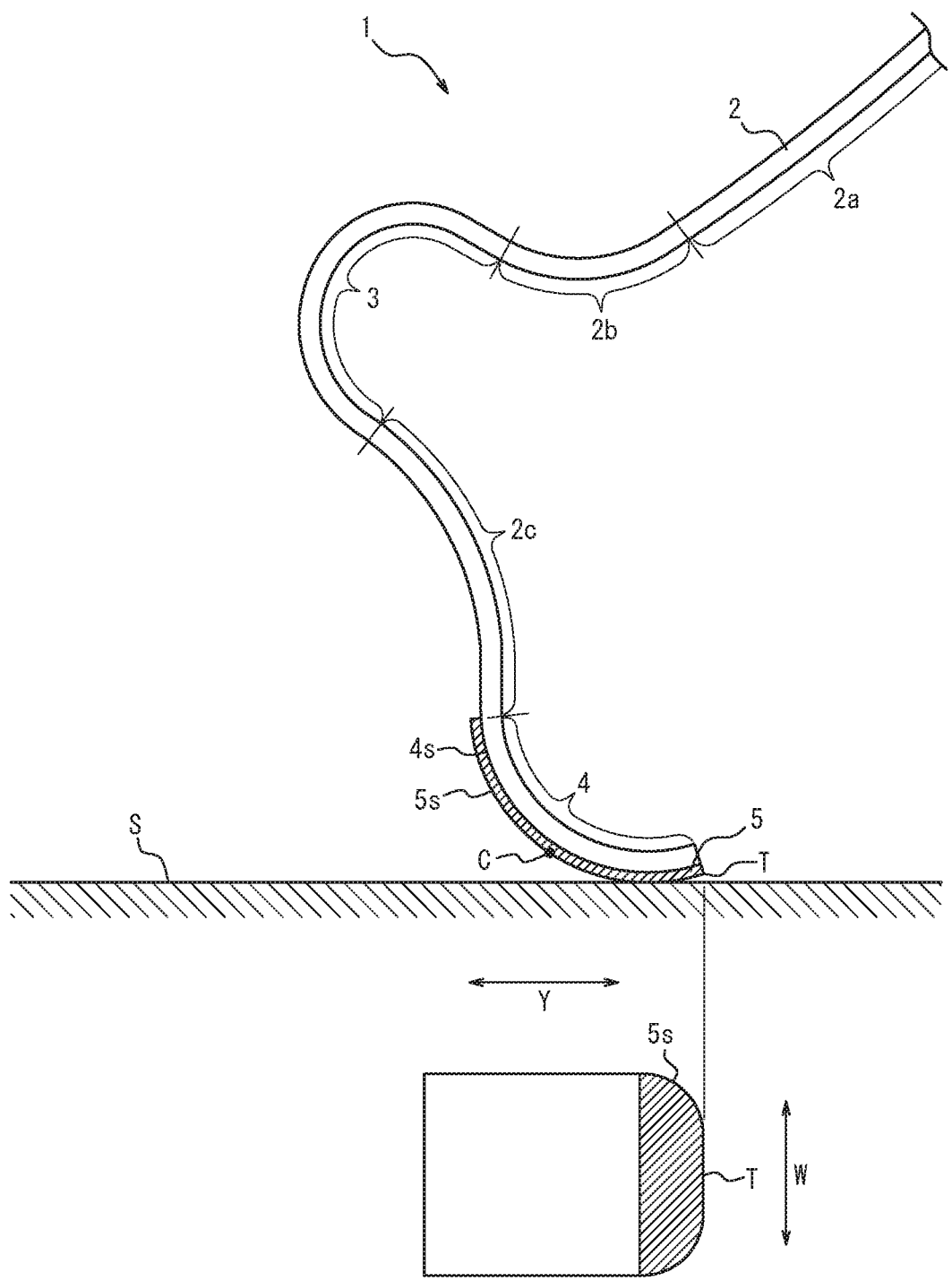
FIG. 2D is a drawing for explaining in stages the movement of the leg portion and the ground contact form in a case where the athletic prosthetic leg is worn and the wearer executes straight running.

FIG. 2D illustrates a state that the wearer is in a final stage of kicking out the athletic prosthetic leg 1 just before separating from the road surface S. To kick out from the toe T of the bottom surface 5s, ground contact is executed further at the side of the toe T than in FIG. 2C.

Figure 3:
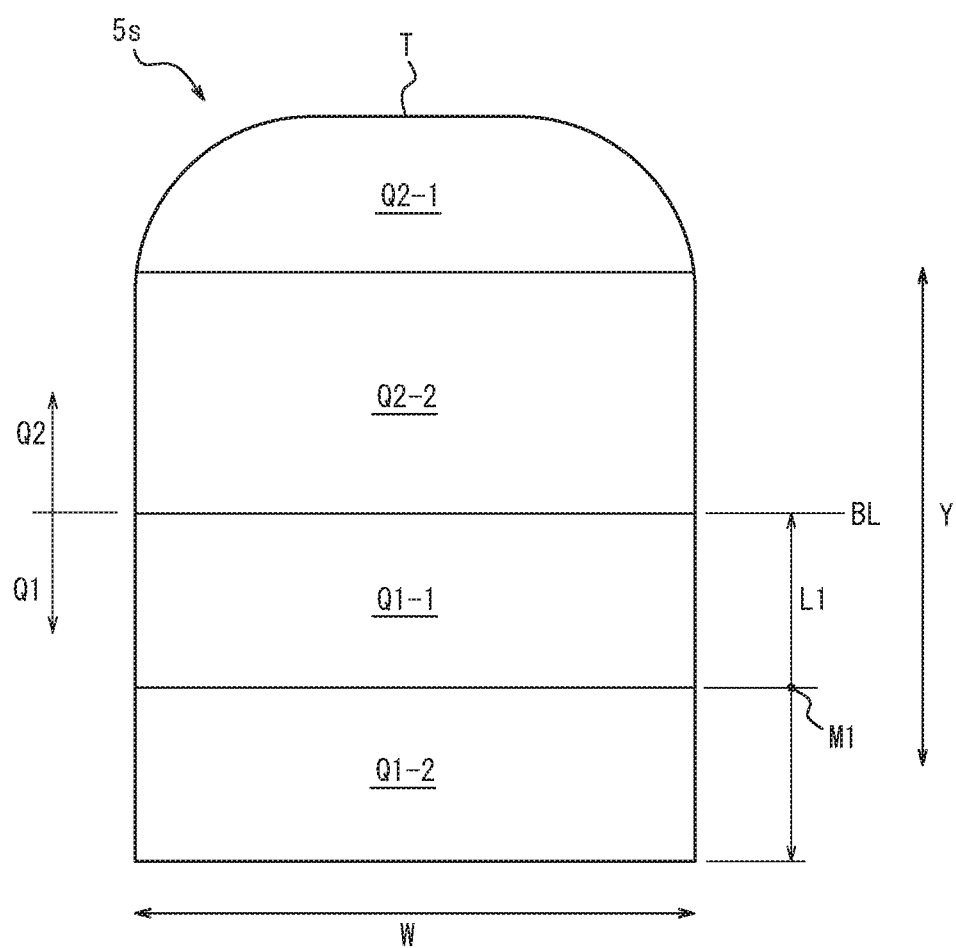
FIG. 3 is a drawing for explaining each region of a bottom surface.

Based on the experimental result illustrated in FIGS. 2A, 2B, 2C and 2D, as illustrated in FIG. 3, firstly, the bottom surface 5s is divided into a curved portion side region Q1 and a toe side region Q2 with a border of the point C. Additionally, FIG. 3 is a drawing for explaining each region of the bottom surface 5s, and the sole bottom surface 5s is illustrated in a plane.

In other words, the curved portion side region Q1 is a region at the side of the curved portion 3 defined by a border as a line BL extending in the width direction W of the leg portion 2 through the point C in the bottom surface 5s. As illustrated in FIGS. 2A and 2B, the curved portion side region Q1 is a region where the wearer firstly contacts the ground and executes a step movement in a state that the entire weight is loaded to the athletic prosthetic leg 1. Consequently, it is vital that the curved portion side region Q1 fully grips the road surface S such that the entire body is balanced even when the entire weight of the wearer is loaded on the athletic prosthetic leg 1. Thus, to prevent slip due to a water film interposed between the bottom surface 5s and the road surface S, drainage performance of the curved portion side region Q1 needs to be higher than a portion other than the curved portion side region Q1, that is, the toe side region Q2.

In other words, since the curved portion side region Q1 has a higher drainage performance compared with the portion other than the curved portion side region Q1, the sole 5 of the athletic prosthetic leg 1 prevents slip due to the water film and achieves a high anti-slip property.

On the other hand, the toe side region Q2 is a region at the side of the toe T defined by the border as the line BL extending in the width direction W of the leg portion 2 through the point C in the bottom surface 5s. The toe side region Q2 is a region where the wearer shakes an opposite leg from a leg wearing the athletic prosthetic leg 1 forward to execute the kick-out 10) movement of the athletic prosthetic leg 1. The toe side region Q2 sequentially contacts the ground toward the toe T, and the wearer presses the road surface S by the bottom surface 5s to slidingly contact the ground, so that the toe side region Q2 is a region which easily develops abrasion in particular. Thus, wear resistance performance of the toe side region Q2 needs to be higher than that of the curved portion side region Q1.

In other words, with the toe side region Q2 having a higher wear resistance performance than the curved portion side region Q1, early abrasion of the toe side region Q2 is avoided, and as a result, the entire surface of the sole 5 of the athletic prosthetic leg 1 is gently worn and a long service life of the sole 5 can be achieved.

Also, it is preferable that each of the curved portion side region Q1 and the toe side region Q2 is further divided as illustrated in FIG. 3 based on the ground contact form illustrated in FIGS. 2A to 2D such that each portion has property corresponding to the ground contact form.

In other words, of the toe side region Q2 illustrated in FIG. 3, a portion Q2-1 corresponds to the arc X1 which continues from the toe T with a constant radius of curvature in FIG. 1. The portion Q2-1 finally contacts the ground when the wearer who wears the athletic prosthetic leg 1 executes the kick-out movement, so that severer abrasion has been inclined to occur. Thus, the portion Q2-1 needs to have an especially high wear resistance performance. In other words, in the toe side region Q2, the portion Q2-1 has a higher wear resistance performance than a remaining portion Q2-2, so that the sole 5 is protected from severe abrasion and the long service life of the leg portion 2 itself can be achieved.

Next, in the curved portion side region Q1, a first side portion Q1-1 at the side of the toe T from a center M1 of a maximum length L1 along the leg portion front-rear direction Y is a region which firstly contacts the ground, so that prevention of slip is especially necessary such that the wearer achieves a balance of his body. Thus, the first side portion Q1-1 preferably has a further higher drainage performance than a second side portion Q1-2 in the curved portion side region Q1 such that slip is more surely prevented and a further stable running is achieved.

Also, the second side portion Q1-2 is a portion at the side of curved portion 3 from the center M1 of the maximum length L1. As illustrated in FIG. 2B, in the curved portion side region Q1, the ground contact portion is changed to the side of the curved portion 3 from the first side portion Q1-1 which firstly contacts the ground, that is, the second side portion Q1-2 at the opposite side from a direction that the wearer advances. At the time of ground contact of the second side portion Q1-2, movement of an upper body in which the wearer tries to move forward and movement of the ground contact portion are temporarily opposite, so that a high propulsive force is needed for the kick-out movement at the latter half of the ground contact form. Consequently, firstly, it is vital that the second side portion Q1-2 has a higher rigidity than the first side portion Q1-1. Since the second side portion Q1-2 has a higher rigidity than the first side portion Q1-1, the step movement is smoothly continued to the kick-out movement, and a high propulsive force can be achieved.

Especially, in a case where the bottom surface 5s includes a pattern constituted by a plurality of recesses and protrusions, the second side portion Q1-2 preferably has a larger edge component in the width direction W of the leg portion 2 than the first side portion Q1-1. Also, a negative ratio of the second side portion Q1-2 is preferably smaller than that of the first side portion Q1-1. Here, the negative ratio refers to a percentage in an area of a recessed portion to the road surface S in a planar view in a total area of the bottom surface 5s in a planar view. With this configuration, a high propulsive force can be exerted in running.

Also, to exert the propulsive force effectively, the second side portion Q1-2 preferably has a larger edge component in the width direction W of the leg portion 2 than the toe side region Q2. Further, a negative ratio of the second side portion Q1-2 is preferably larger than that of the toe side region Q2. With this configuration, the second side portion Q1-2 can exert a high propulsive force when the wearer executes the kick-out movement.

Concrete means to achieve the above-described properties to be applied to each portion of the bottom surface 5s includes, for example, designing a pattern constituted by recesses and protrusions by grooves and the like formed on the bottom surface 5s, designing the surface property of the bottom surface 5s, designing the cross-sectional shape of the sole 5 and 10) designing the material of the sole 5.

Figure 4:
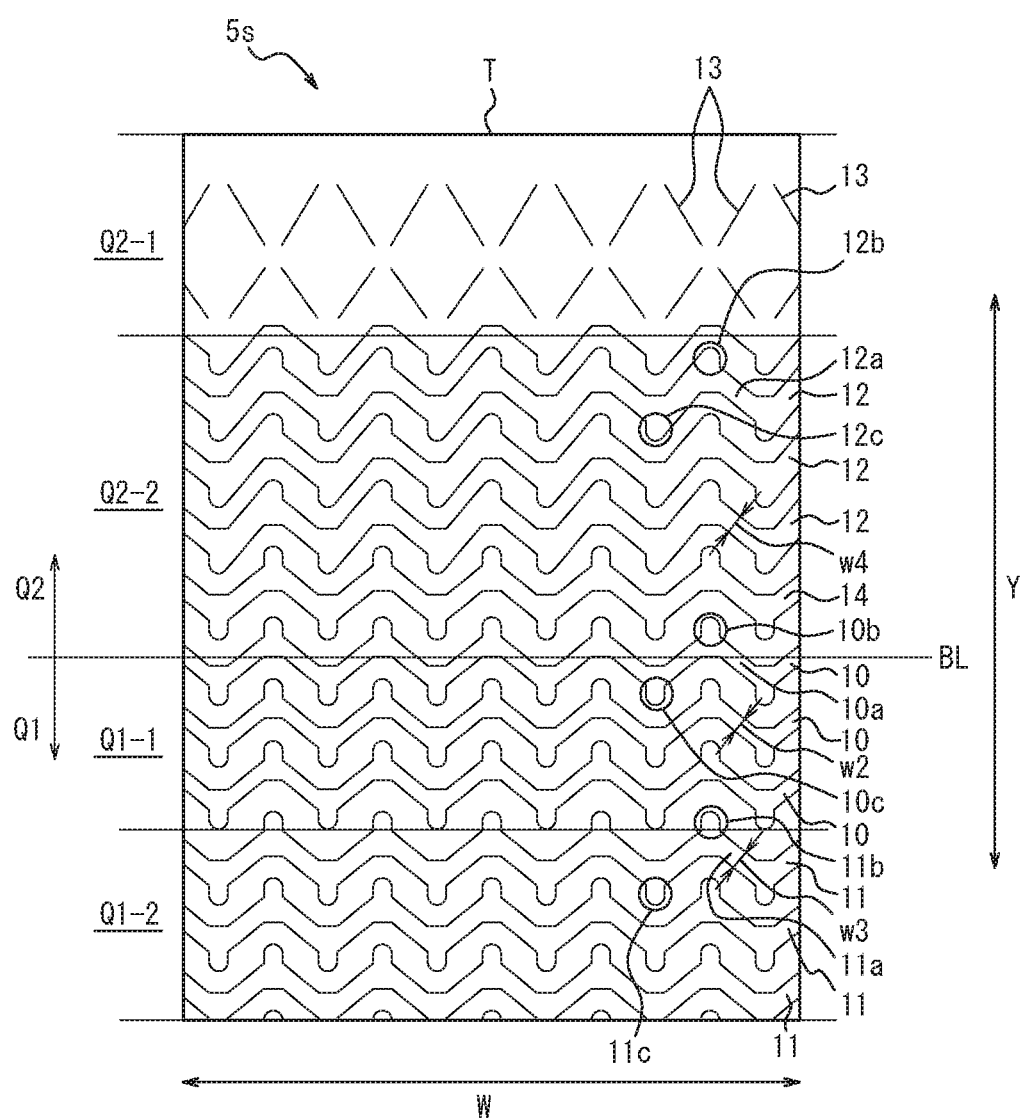
FIG. 4 is a drawing which illustrates a pattern of the bottom surface of the sole of the athletic prosthetic leg according to the first embodiment.

Hereinafter, firstly, the first embodiment and a second embodiment will be explained about a case where each function is applied by design of the pattern constituted by recesses and protrusions of the bottom surface 5s. FIG. 4 is a drawing which illustrates a pattern of the bottom surface 5s of the sole 5 in the athletic prosthetic leg 1 according to this embodiment.

In the pattern illustrated in FIG. 4, a plurality of land portions 10 and a plurality of land portions 11 which are defined by a plurality of grooves extending in the width direction W are arranged in the curved portion side region Q1. The land portions 10 are arranged to the side of the toe T from the land portions 11. The land portions 10 are shaped to include a width direction extending portion 10a extending in the width direction W to be substantially zigzag-shaped, a first bent portion 10b (toe side protruding portion 10b) extending to the side of the toe T from a bent portion bending to be convex to the side of the toe T and a second bent portion 10c (curved portion side protruding portion 10c) extending to the side of the curved portion from a bent portion bending to be convex to the side of the curved portion 3. The land portions 11 are shaped to include a width direction extending portion 11a, a first bent portion 11b (toe side protruding portion 11b) and a second bent portion 11c (curved portion side protruding portion 11c). The width direction extending portions 10a and 11a are zig-zag shaped, thereby fully ensuring the edge component. Further, by forming the first bent portions 10b and 11b as well as the second bent portions 10c and 11c, the edge component is further increased, and the water film interposed between the bottom surface 5s and the road surface S can be efficiently cut on both sides in the leg portion front-rear direction Y, thereby achieving a high drainage performance.

Also, in FIG. 4, a plurality of land portions 12 which are defined by a plurality of grooves extending in the width direction W are arranged in the toe side region Q2. The land portions 12 are shaped to include a width direction extending portion 12a extending in the width direction W to be substantially zig-zag shaped, a first bent portion 12b (toe T side protruding portion 12b) extending to be convex in a direction that the width direction extending portion 12a extends from a bent portion bending to be convex to the side of the toe T and a second bent portion 12c (curved portion side protruding portion 12c) extending to be convex in a direction that the width direction extending portion 12a extends from a bent portion bending to be convex to the side of the curved portion 3. Further, a plurality of linear grooves 13 intermittently extending along the zig-zag shape extending in the width direction W are formed in the toe side region Q2. The land portions 12 are arranged to the side of the curved portion 3 from the linear grooves 13 and the linear grooves 13 are formed to the side of the toe T from the land portions 12. Additionally, as illustrated in the drawing, a land portion 14 having the same shape as the land portions 11 may be formed in the toe side region Q2.

In FIG. 4, a land portion width w2 of the width direction extending portion 10a of the land portions 10 is larger than a land portion width w3 of the width direction extending portion 11a of the land portions 11. Also, a land portion width w4 of the width direction extending portion 12a of the land portions 12 is larger than the land portion widths w2 and w3.

In this configuration, in the curved portion side region Q1, a percentage in an area of a groove portion which is concave to the road surface S in a planar view in a total area of the bottom surface 5s in a planar view, that is, a negative ratio is larger than that in the toe side region Q2. Thus, in the curved portion side region Q1, more water can be taken in a recessed groove and can be discharged. Thus, the curved portion side region Q1 has a higher drainage performance than the toe side region Q2.

On the other hand, the toe side region Q2 has a higher wear resistance performance than the curved portion side region Q1. The reason is that the toe side region Q2 has a smaller negative ratio than the curved portion side region Q1 to maintain a high rigidity.

Additionally, in the toe side region Q2, the linear groove 13 is formed in the portion Q2-1. With this configuration, the ground contact portion Q2-1 has a larger rigidity than the remaining portion Q2-2 in the toe side region Q2 to include a further higher wear resistance performance.

Also, in FIG. 4, in the curved portion side region Q1, the negative ratio of the first side portion Q1-1 is larger than that of the second side portion Q1-2, so that more water can be taken in the grooves and can be discharged. In other words, the first side portion Q1-1 has a further higher drainage performance than the second side portion Q1-2.

Further, in the curved portion side region Q1, the land portions 11 are arranged in the second side portion Q1-2. Moreover, as described before, the land portion width w3 of the land portions 11 is larger than the land portion width w2 of the land portions 10. Thus, the second side portion Q1-2 has a larger land portion rigidity than the first side portion Q1-1. Further, the second side portion Q1-2 has a larger edge component in the width direction W than the first side portion Q1-1. Also, as described before, the negative ratio of the second side portion Q1-2 is smaller than that of the first side portion Q1-1.

Also, the second side portion Q1-2 has a larger edge component in the width direction W than the toe side region Q2 and further, has a larger negative ratio.

Next, a sole of an athletic prosthetic leg according to the second embodiment of the present disclosure will be explained with reference to FIG. 5. In the sole of the athletic prosthetic leg according to the second embodiment, properties included by each portion of the sole are the same as in the first embodiment.

Figure 5:
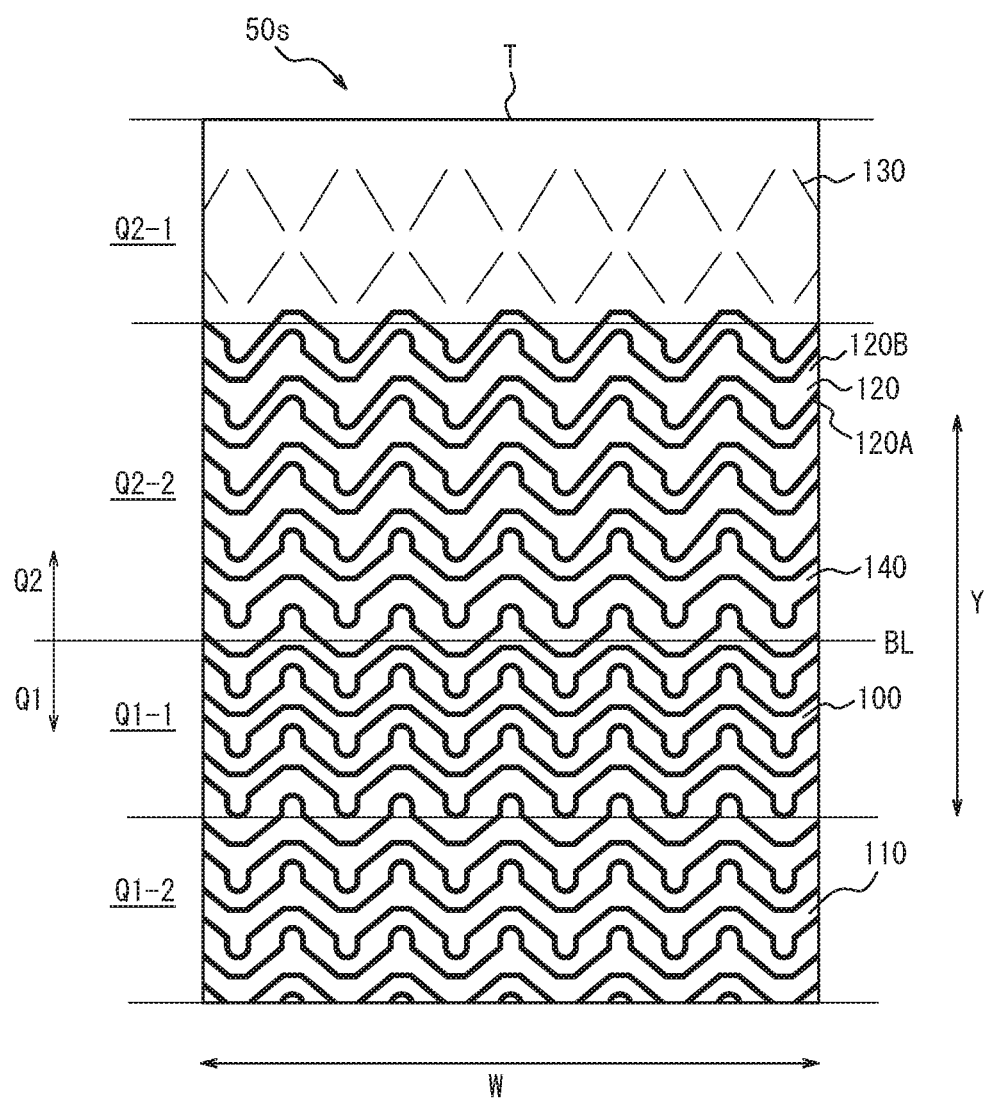
FIG. 5 is a drawing which illustrates a pattern of the bottom surface of the sole of the athletic prosthetic leg according to a second embodiment.

In a bottom surface 50s of the sole 5 illustrated in FIG. 5, a plurality of land portions 100, 110, 120 and 140 which are defined by a plurality of grooves extending in the width direction W are arranged. The land portions 100, 110, 120 and 140 correspond to the land portions 10, 11, 12 and 14 illustrated in FIG. 4. While the same shape as that of the corresponding land portion is illustrated in a planar view of the bottom surface 50s, in a depth direction of the grooves defining each land portion, the land portions 100, 110, 120 and 140 have a two-stage structure. The two-stage structure will be explained with reference to the land portions 120. The land portions 120 have a step-like structure in which a second-stage block 120B is located above a first-stage block 120A at the side of the groove bottom in a thickness direction of the sole 5. A stepped portion of the first-stage block 120A is illustrated by a thick line in the drawing. While the second-stage block 120B has a smaller surface area than the first-stage block 120A in a planar view, the second-stage block 120B and the first-stage block 120A has the 10) same shape. In a case where the wearer who wears the athletic prosthetic leg 1 executes straight running movement, when the second-stage block 120B firstly contacts the ground to be crushed, water interposed between the first-stage block 120A and the road surface S is pushed out to the side of the road surface S, thereby discharging the water effectively. Further, the first-stage block 120A contacts the ground after the second-stage block 120B, which fully ensures a foot print area with the road surface S while drainage performance is not deteriorated. The land portions 100, 110 and 140 also include stepped portions illustrated by a thick line and have the step-like structure.

Next, a sole of an athletic prosthetic leg according to a third embodiment of the present disclosure will be explained with reference to FIG. 6. In a bottom surface 500s of the sole 5 of the athletic prosthetic leg according to the third embodiment, a plurality of land portions 15 each having the shape of a square with rounded corners in a planar view are defined by forming a recessed groove in the first side portion Q1-1 of the curved portion side region Q1. Also, land portions 16a and 16b are arranged at the side of the curved portion 3 from the land portions 15 in the curved portion side region Q1. The land portions 16a and 16b are applied the shape of a square with rounded corners in a planar view by forming a recessed groove in the bottom surface 500s, and have a larger area in the planar view than the land portions 15. Also, the land portion 16b has a larger area in a planar view than the land portion 16a. Further, land portions 17a and 17b having the same shape as the land portions 16a and 16b are defined also in the toe side region Q2. Further, a land portion 18a having the shape of a rectangle with rounded corners in a planar view is formed in the toe side region Q2 at the side of the toe T from the land portions 17a and 17b, and a semi-land portion 18b is defined at the side of the toe T from the land portion 18a in an aspect that a depth of the groove is tapered toward the side of the toe T. Moreover, a plurality of linear grooves 19a and a plurality of linear grooves 19b which are inclined to the width direction W are continuously arranged along the width direction W at the side of the toe T from the semi-land portion 18b. The linear grooves 19a and the linear grooves 19b are inclined in an opposite direction from each other to the width direction W.

Figure 6:
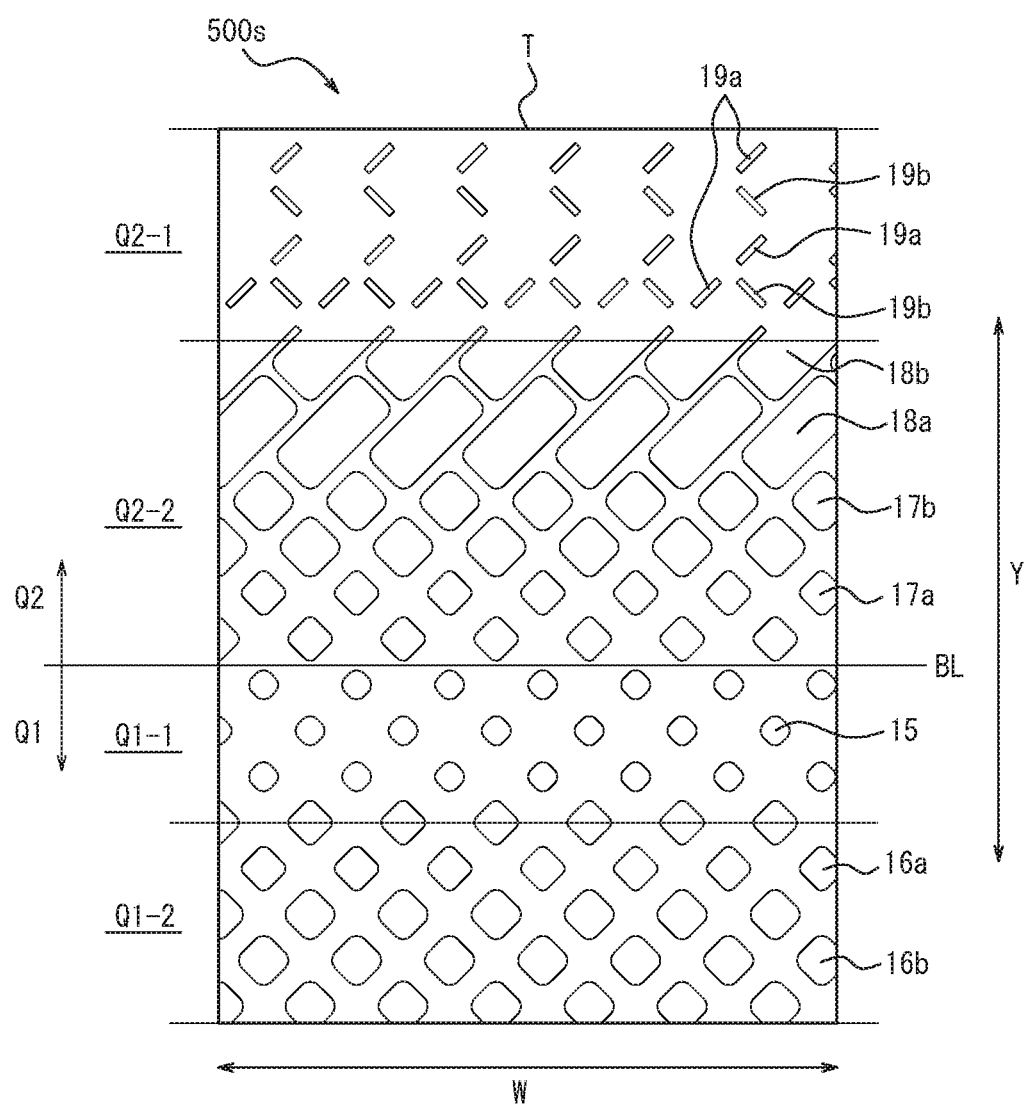
FIG. 6 is a drawing which illustrates a pattern of the bottom surface of the sole of the athletic prosthetic leg according to a third embodiment.

With this configuration, the curved portion side region Q1 and the toe side region Q2 illustrated in FIG. 6 can apply the same function as the curved portion side region Q1 and the toe side region Q2 in the sole of the athletic prosthetic leg according to the first embodiment and the second embodiment.

Figure 7:
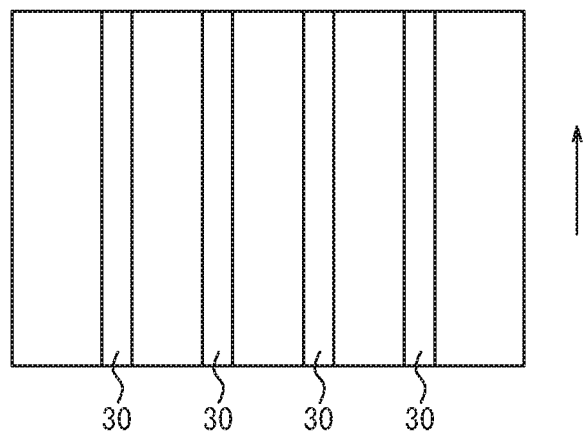
FIG. 7 is a drawing which schematically illustrates a pattern element constituting a pattern by recesses and protrusions.
Figure 8:
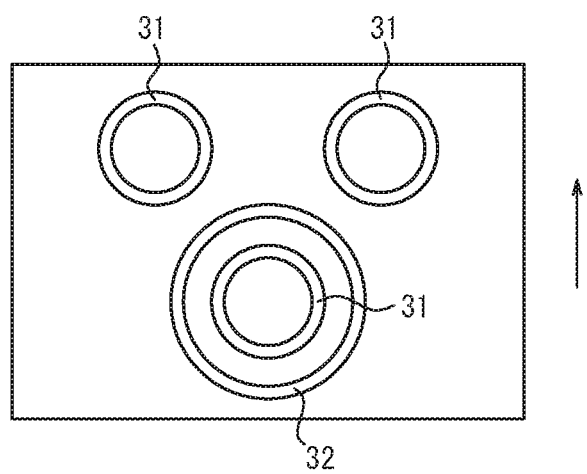
FIG. 8 is a drawing which schematically illustrates a pattern element constituting a pattern by recesses and protrusions.

Additionally, in the case where each function is applied by the pattern constituted by recesses and protrusions of the bottom surface of the sole 5, the pattern is not limited to ones in the embodiments, and patterns illustrated below can be used. Each pattern will be explained with reference to FIGS. 7, 8 and 9. Additionally, FIGS. 7 and 8 schematically illustrate pattern elements constituting a pattern by recesses and protrusions. By varying the number of the pattern elements or the specification thereof for every region or portion described above, a function required for each region and each portion can be applied.

For example, as illustrated in FIG. 7, a pattern in which a plurality of vertical grooves 30 extending along the leg portion front-rear direction Y are formed can be used. With this configuration, water taken in the vertical grooves 30 flows accompanied with movement of the sole, so that the water can be efficiently discharged from an end portion of the vertical grooves 30. By varying the width or the depth of the vertical grooves 30 for each portion of the bottom surface of the sole 5, a pattern which prioritizes any of drainage performance and wear resistance performance can be applied.

Also, as illustrated in FIG. 8, a pattern in which a plurality of grooves 31 and 32 continuing annularly are formed can be used. Due to the annular grooves 31 and 32, intake and discharge of water can be efficiently executed irrespective of a direction of various inputs of force acting on the bottom surface of the sole 5. By varying the width, depth or diameter of a ring of the annular grooves 31 and 32 for each portion of the bottom surface 5s, a pattern which prioritizes any of drainage performance and wear resistance can be applied.

Additionally, the bottom surface of the sole 5 may have a pattern in which only the vertical grooves or the only the annular grooves are formed, or a pattern with a combination of the vertical grooves and the annular grooves. Further, a pattern with a combination of the annular grooves and lateral grooves may be applied.

Figure 9A:
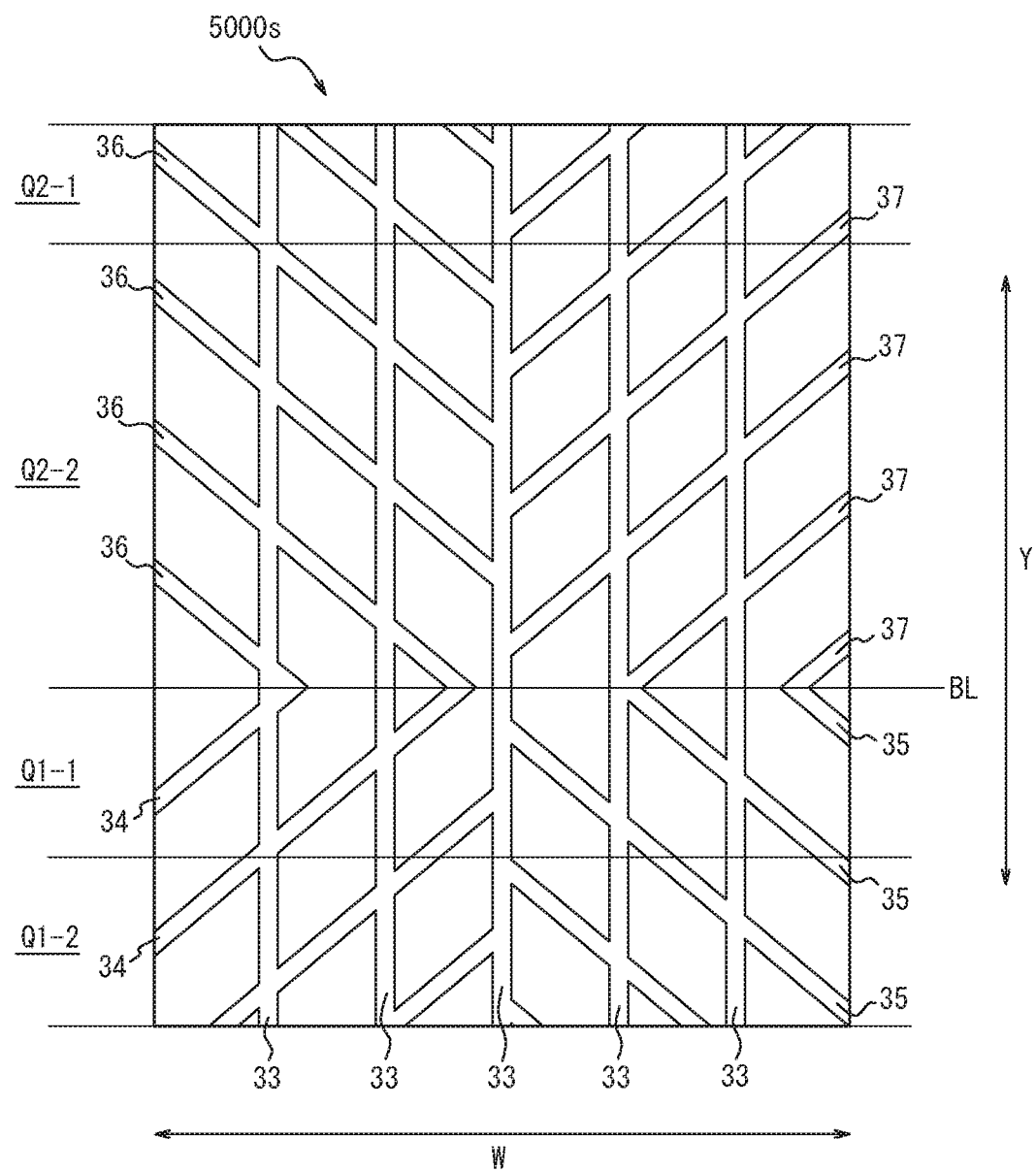
FIG. 9A is a drawing which illustrates the bottom surface of the sole to which a pattern by recesses and protrusions is applied.
Figure 9B:
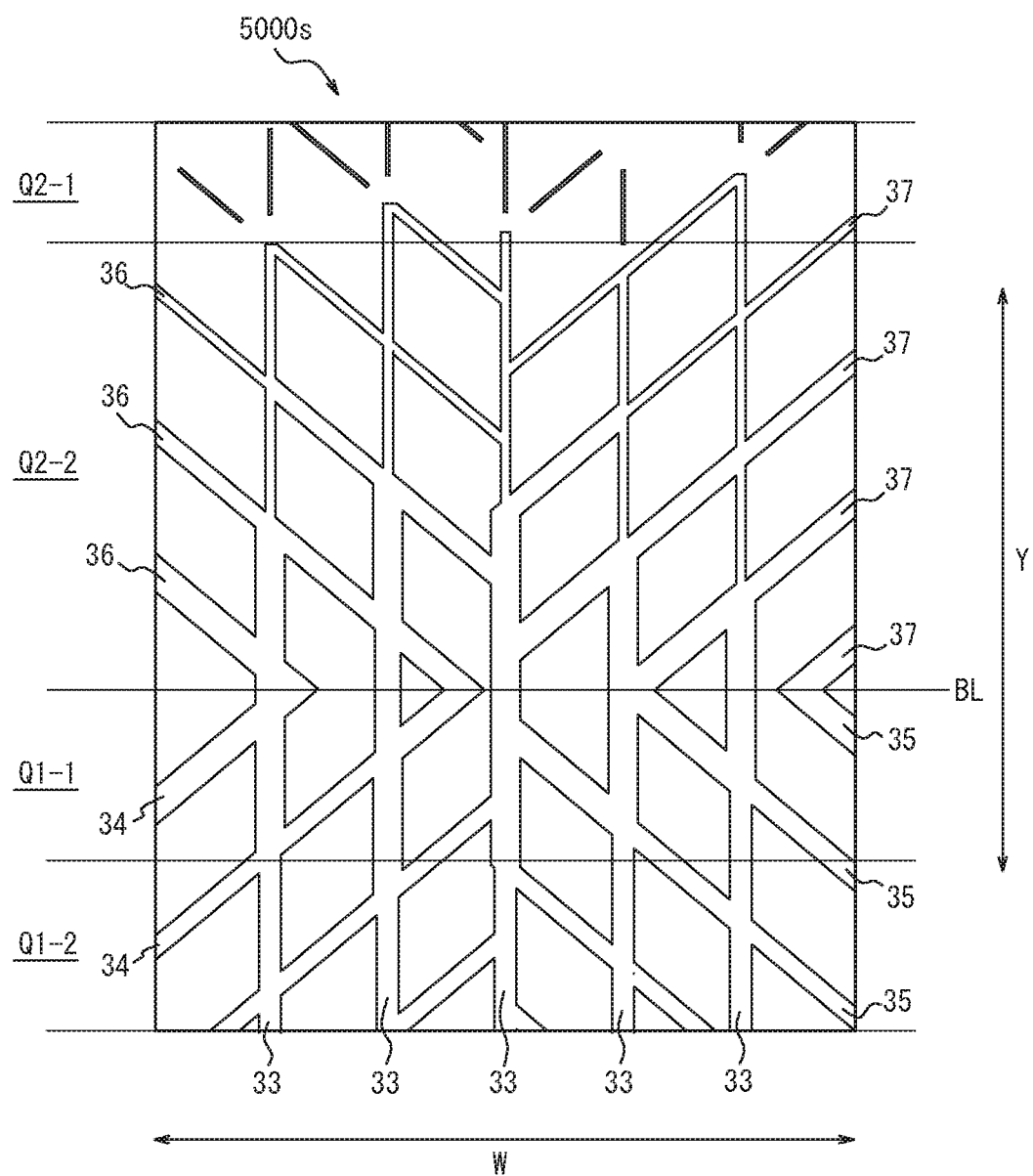
FIG. 9B is a drawing which illustrates the bottom surface of the sole to which a pattern by recesses and protrusions is applied.

Further, as a pattern of the bottom surface of the sole 5, a pattern illustrated in FIG. 9A or 9B can be used. In this pattern, in a bottom surface 5000s of the sole 5, a plurality of vertical grooves 33 which are open at one end or both ends are formed at sole end edges at the side of the toe T as well as the side of the curved portion 3, and a plurality of inclined grooves 34, 35, 36 and 37 which communicate with the vertical grooves 33, inclinedly extend in the width direction W and are open at the sole end edges are formed. As illustrated in the drawing, in the curved portion side region Q1, the inclined grooves 34, 35 extend inclinedly to the side of the curved portion 3 from the center in the width direction W of the bottom surface 5000s toward the sole end edges. On the other hand, in the toe side region Q2, the inclined grooves 36, 37 extend inclinedly to the side of the toe T from the center in the width direction W of the bottom surface 5000s toward the sole end edges. With this configuration, drainage performance in accordance with the ground contact form of the athletic prosthetic leg 1 can be achieved. In other words, in the bottom surface 5000s, a ground contact portion is changed to the second side portion Q1-2 at the side of the curved portion 3 from the first side portion Q1-1 which firstly contacts the ground. In accordance with a transition movement, water taken in the grooves flows along the inclination of the grooves from the side of toe T to the side of the curved portion 3, and is discharged from an opening at an end edge of the bottom surface 5000s. Further, accompanied with a transition movement of the ground contact portion from the curved portion side region Q1 to the toe side region Q2, the water taken in the grooves flows along the inclination of the grooves from the side of the curved portion 3 to the side of the toe T, and is discharged from an opening at an end edge of the sole 5. With this operation, efficient drainage can be achieved. While the groove width of each groove is constant in FIG. 9A, in FIG. 9B, the groove width is enlarged in a region in which drainage performance is prioritized, while the groove width is reduced in a region in which wear resistance performance is prioritized.

Additionally, in any of the examples explained so far, the depth of the groove and the number of grooves formed at the bottom surface of the sole 5 is arbitrary. By enlarging the depth of the groove, the drainage performance can be more improved. Further, the drainage performance can be also 10) improved by increasing the number of grooves.

Also, in addition to improvement of the drainage performance of the entire bottom surface of the sole 5 due to the patterns explained so far, the wear resistance performance and the drainage performance can be controlled for each region and each portion by designing the surface property of the bottom surface of the sole 5, for example, varying the introduction density of a sipe, the surface roughness and a riblet and the like illustrated below.

For example, the drainage performance can be improved by forming a plurality of sipes which is narrower than grooves on the bottom surface of the sole 5. The more the number of the sipes increases, the higher the drainage performance can be obtained. As for the wear resistance performance, this relation may be reversed. The same comment is applied to the surface roughness and the riblet below.

The surface roughness is adjusted by applying micro recesses and protrusions to the bottom surface of the sole 5, thereby improving the drainage performance and the wear resistance performance. When a coarser surface roughness is used, water can be taken in the micro recesses and protrusions, so that a high drainage performance can be achieved.

Also, by providing so-called riblets in which fine grooves are continuously aligned in the width direction W or the leg portion front-rear direction Y, water interposed between the road surface S and the sole 5 sequentially infiltrates each narrow groove of the riblet due to capillary action, so that a higher drainage performance can be achieved.

Further, by providing water repellent finishing to a surface of the bottom surface of the sole 5, water applied to a surface of the bottom surface of the sole 5 can be efficiently eliminated, so that the drainage performance can be improved.

Figure 10A:
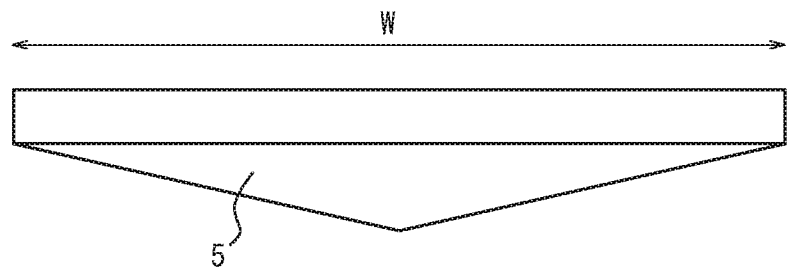
FIG. 10A is a schematic cross-sectional view along a width direction of the leg portion of the sole.
Figure 10B:
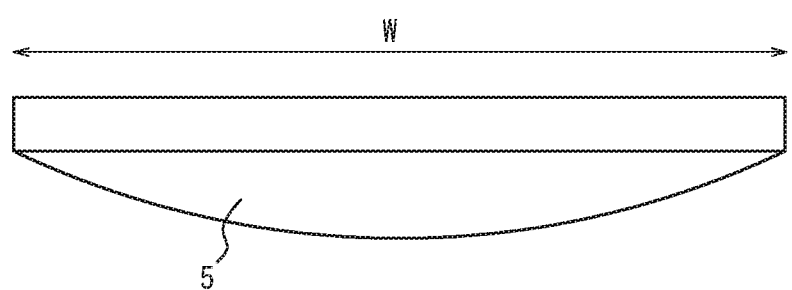
FIG. 10B is a schematic cross-sectional view along the width direction of the leg portion of the sole.
Figure 10C:
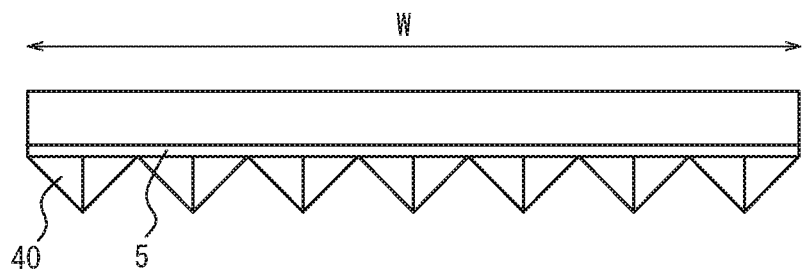
FIG. 10C is a schematic cross-sectional view along the width direction of the leg portion of the sole.

Next, a case where each function is applied by designing the cross-sectional shape of the sole 5 will be explained. FIGS. 10A, 10B and 10C are schematic cross-sectional views along the width direction W of the sole 5.

In FIGS. 10A and 10B, the thickness of the sole 5 is largest at the center in the width direction W, and it is tapered toward the side of the sole end edge in the width direction W. The sole 5 may have the shape in which the thickness is linearly tapered as illustrated in FIG. 10A, while it may have the shape in which the thickness is tapered in an arc as illustrated in FIG. 10B. With this configuration, at the time of ground contact of the bottom surface 5s, water on the road surface S is pushed out from the center side in the width direction W of the sole 5 to the side of the sole end edge, so that efficient drainage can be executed. Additionally, the entire sole 5 may have this configuration, or only a part of the sole 5 may have this configuration.

Also, as illustrated in FIG. 10C, the sole 5 may have a structure that it has a plurality of cones which are convex to the ground contact side. In the illustrated example, the sole 5 has a plurality of quadrangular pyramids 40 which are convex to the ground contact side. With this configuration, due to the plurality of quadrangular pyramids 40, the bottom surface of the sole 5 is spike-like, which achieves ground contact from an apex by efficiently cutting a water film existing between the bottom surface of the sole 5 and the road surface S. Consequently, a high drainage performance can be achieved. Moreover, since the water can pass through a gap formed between the plurality of quadrangular pyramids 40, a high drainage performance can be achieved. Additionally, not limited to a quadrangular pyramid, a cone or polygonal cones other than a quadrangular pyramid may be applied. Moreover, wear resistance performance can also be achieved by varying the size of a pyramid in accordance with each region of the bottom surface of the sole 5.

Figure 11A:
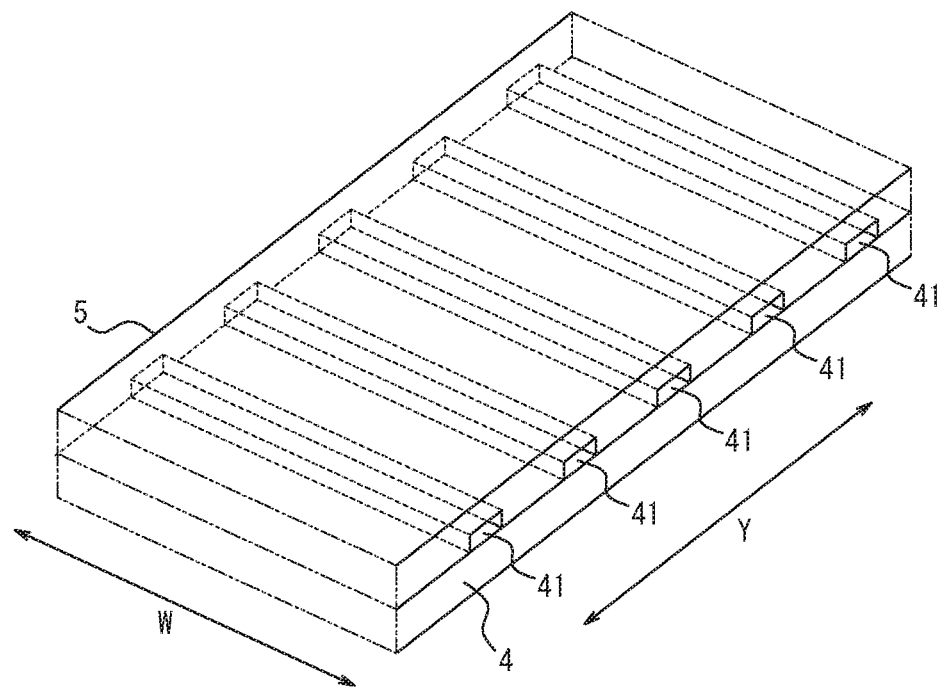
FIG. 11A is a perspective view which illustrates a ground contact portion and the sole.
Figure 11B:
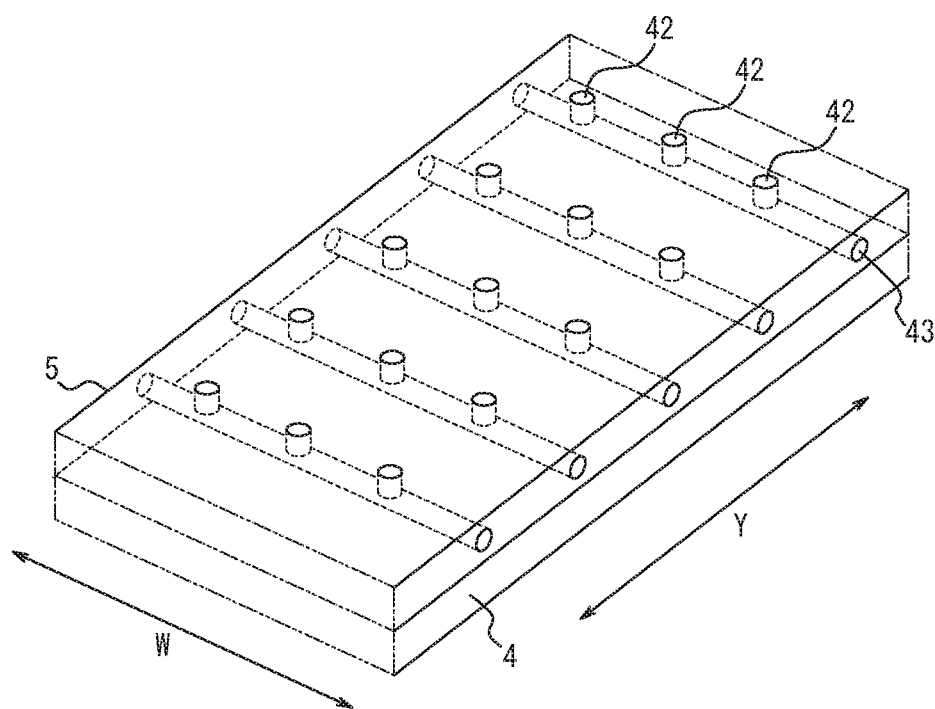
FIG. 11B is a perspective view which illustrates the ground contact portion and the sole.

FIGS. 11A and 11B are perspective views illustrating the ground contact portion 4 and the sole 5. As illustrated in FIG. 11A, the sole 5 has a hidden groove 41 which is open to the side of the ground contact portion 4 at the side of a border surface between the ground contact portion 4 and the sole 5. The hidden groove 41 extends along the width direction W to be open at both end edges of the sole 5. With this configuration, water on the road surface is taken in the hidden groove 41 from both ends of the leg portion 2 in the width direction W and discharged. This prevents the water from infiltrating a portion between the bottom surface of the sole 5 and the road surface S, so that a high drainage performance can be obtained. Additionally, although not illustrated in FIG. 11A, in a case where an adhesive is interposed between the ground contact portion 4 and the sole 5, the sole 5 is formed with a groove or a recess portion which is open to the 10) side of the adhesive at the side of a border surface with the adhesive.

Also, as illustrated in FIG. 11B, the sole 5 may have the configuration that includes a combined groove in which a circular groove 42 formed on the bottom surface of the sole 5 communicates with a groove 43 penetrating through the sole 5 along the width direction W. With this configuration, water interposed between the bottom surface of the sole 5 and the road surface S can be taken in from the circular groove 42 and can be discharged efficiently from an end portion of the groove 43 penetrating in the width direction W. Also, by combining such combined groove with a groove constituted by recesses and protrusions at the bottom surface of the sole 5, rigidity of the sole 5 can be adjusted and property in accordance with each region of the bottom surface of the sole 5 can be applied.

Subsequently, a case where each function is applied by designing a part or the entire of the material of the sole 5 will be explained. For example, felt, a sponge or non-woven fabric is used to a part or the entire of the sole 5 and drainage performance can be improved due to a water absorption operation of each material. Also, the same effect can be obtained by using foamed rubber to a part or the entire of the sole 5 due to a water abrasion operation of the foamed rubber.

Additionally, the sole 5 of the athletic prosthetic leg 1 according to the present disclosure explained so far can be manufactured, for example, by a method of processing a rubber sheet by a laser light, a method of using a mold and a manufacturing method using a 3D printer.

Also, in the athletic prosthetic leg 1 according to the present disclosure, the sole 5 is attached to the ground contact region 4s via an adhesive. However, attachment means is not limited to the adhesive, and attachment may be executed using fasteners such as a belt. Further, in the present disclosure, while the sole 5 is attached to the ground contact region 4s by directly abutting, a cushion member (not shown) or a binding material may be interposed between the sole 5 and the ground contact region 4s.

Figure 12A:
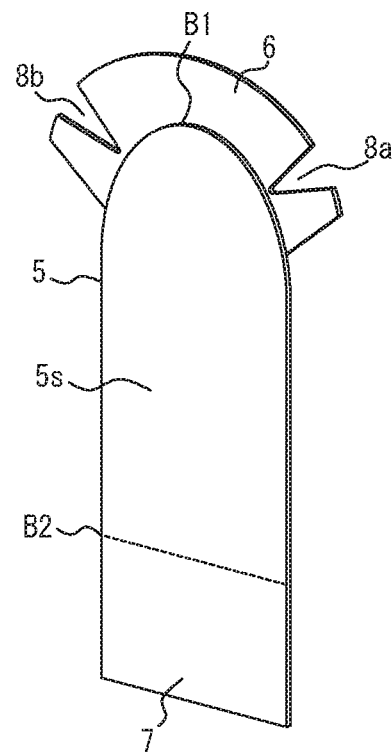
FIG. 12A is a perspective view which illustrates the sole and a tab for sticking before the sole is mounted to the ground contact portion.
Figure 12B:
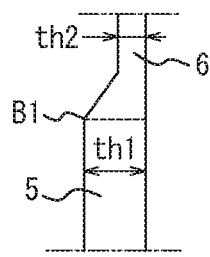
FIG. 12B is a drawing for explaining the thicknesses at a border between a toe-side tab for sticking and the sole and at a portion adjacent to the border.
Figure 12C:
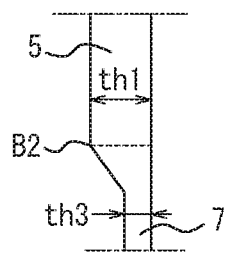
FIG. 12C is a drawing for explaining the thicknesses at a border between a curved-portion-side tab for sticking and the sole and at a portion adjacent to the border.

Here, an example of attachment means of the sole 5 will be explained below with reference to FIGS. 12A, 12B and 12C. FIG. 12A is a perspective view which illustrates the sole 5 and a tab for sticking before the sole 5 is attached to the ground contact portion 4. Additionally, in FIG. 12A, a pattern of the bottom surface 5s is omitted. As illustrated, a toe-side tab for sticking 6 and a curved-portion-side tab for sticking 7 are integrally connected to the sole 5. The toe-side tab for sticking 6 is fan-shaped and connected along an end edge at the side of the toe T of the sole 5, and moreover, is divided by two cuts 8a, 8b. Moreover, the curved-portion-side tab for sticking 7 is connected to an end edge at the side of the curved portion 3 of the sole 5. FIG. 12B is a drawing for explaining thicknesses at a border between the toe-side tab for sticking 6 and the sole 5 and at a portion adjacent to the border. In addition, FIG. 12C is a drawing for explaining the thicknesses at a border between the curved-portion-side tab for sticking 7 and the sole 5 and at a portion adjacent to the border. As illustrated in FIG. 12B, the toe-side tab for sticking 6 extends with a constant thickness th2 which is thinner than a thickness th1 of the sole 5, and the thickness gradually increases toward a border B1 with the sole 5. Also, the curved-portion-side tab for sticking 7 extends with a thickness th3 which is thinner than the thickness th1 of the sole 5, and the thickness gradually increases toward a border B2 with the sole 5. With this configuration, when the sole is attached to the ground contact portion 4, close attachment can be executed without any deflection or gap between the sole 5 and the ground contact portion 4. For example, assuming that the thickness th1 of the sole 5 is 2.25 to 3.0 mm, the thickness th2 of the toe-side tab for sticking 6 and the thickness th3 of the curved-portion-side tab for sticking 7 may be 1.5 to 2.0 mm.

EXAMPLES

While Examples of the present disclosure will be explained hereinafter, the present disclosure is not limited to this.

Prototypes are produced for each of soles of Examples and soles of comparative examples, and performance evaluation is executed. The soles of Examples are applied a function such as drainage performance specified in the present disclosure due to variation of an arrangement of the pattern or the grooves of the bottom surface of the sole. Of the soles of comparative examples, in a comparative example 1, a pattern of the sole is uniform at the bottom surface. Also, in a comparable example 2, a pattern is different from that of the present disclosure.

As for drainage performance and wear resistance performance, assuming that an index of Q1-1 of the comparative example 1 is 100, it is presented that the drainage performance and the wear resistance performance of the corresponding portion are excellent as the indexes increase.

The sole of comparative examples and the sole of Examples produced experimentally as described above are attached to the athletic prosthetic leg illustrated in FIG. 1 to evaluate anti-slip property and wear resistance performance.

In the comparative example 1 and Example 4, drainage performance and wear resistance performance of each portion of each of the regions Q1, Q2 are evaluated from a result of calculation by simulation. Also, in the comparative example 2 and Examples 1 to 3, the drainage performance and the wear resistance performance of each portion of each of the regions Q1, Q2 are evaluated by the same method as in the comparative example 1 and Example 4.

[Anti-Slip Property]

In a state that a water film of 1 mm is filled on a glass surface and a load of 980N is applied to an athletic prosthetic leg, the following test is executed. A spring scale is attached to a connection portion of the athletic prosthetic leg and a stump of a leg, and the athletic prosthetic leg is pulled to the side of the toe in the leg portion front-rear direction by the spring scale. At the time when the athletic prosthetic leg starts to slip, indexation of a value of the spring scale is executed.

Additionally, assuming that an index of the comparative example 1 is 100, it is presented that anti-slip property is excellent as the index increases.

[Wear Resistance Performance]

A player with a healthy left leg wears an athletic prosthetic leg at a right side, and executes 200 km running on a public road, and thereafter, indexation of an appearance of the entire bottom surface is executed. Additionally, assuming that an index of the comparative example 1 is 100, it is presented that the sole has an excellent wear resistance performance as the index increases. In the comparative example 1 and Example 4, a player with a healthy left leg wore the athletic prosthetic leg at a right side, and executed 200 km running on a public road, and thereafter, indexation of an appearance of the entire bottom surface was executed. Also, in the comparative example 2 and Examples 1 to 3, indexation of the appearance of the entire bottom surface is executed by the same method as in the comparative example 1 and Example 4.

TABLE 1

|  |  |  | Comparative example 1 | Comparative example 2 | Example 1 | Example 2 | Example 3 | Example 4 |
|---|---|---|---|---|---|---|---|---|
| Drainage performance | Curved portion side region Q1 | Portion Q1-1 | 100 | 100 | 110 | 110 | 110 | 120 |
|  |  | Portion Q1-2 | 100 | 100 | 110 | 110 | 110 | 110 |
|  | Toe side region Q2 | Portion Q2-1 | 100 | 110 | 80 | 90 | 90 | 90 |
|  |  | Portion Q2-2 | 100 | 110 | 50 | 90 | 90 | 90 |
| Wear resistance performance | Curved portion side region Q1 | Portion Q1-1 | 100 | 100 | 80 | 80 | 100 | 100 |
|  |  | Portion Q1-2 | 100 | 100 | 100 | 100 | 100 | 100 |
|  | Toe side region Q2 | Portion Q2-1 | 100 | 90 | 100 | 150 | 200 | 200 |
|  |  | Portion Q2-2 | 100 | 90 | 100 | 150 | 150 | 150 |
|  | Anti-slip performance |  | 100 | 103 | 110 | 110 | 110 | 120 |
|  | Wear resistance performance |  | 100 | 90 | 100 | 150 | 160 | 160 |

REFERENCE SIGNS LIST

1 athletic prosthetic leg
2 leg portion
2a straight portion
2b, 2c curved portion
3 curved portion
4 ground contact portion
4s ground contact region
5 sole
5s, 50s, 500s, 5000s bottom surface
6 toe-side tab for sticking
7 curved-portion-side tab for sticking
8a, 8b cut
10, 11, 12, 14 land portion
10a, 11a, 12a width direction extending portion
10b, 11b, 12b first bent portion (toe side protruding portion)
10c, 11c, 12c second bent portion (curved portion side protruding portion)
13, 130 linear groove
100, 110, 120, 140 land portion
15, 16a, 16b, 17a, 17b, 18a land portion
18b semi-land portion
19a, 19b linear groove X1, X2 arc
Q1 curved portion side region
Q2 toe side region
Q1-1 first side portion
Q1-2 second side portion
Q2-1, Q2-2 portion
30 vertical groove
31, 32 groove
33 vertical groove
34, 35, 36, 37 inclined groove
40 quadrangular pyramid
41 hidden groove
42, 43 groove.

The invention claimed is:

1. A sole configured to be attached to a ground contact portion of an athletic prosthetic leg, the athletic prosthetic leg having a base end to be connected to a wearer's leg via an adapter and a socket, a straight portion extending from the base end, a toe end, and a leaf-spring portion extending from the straight portion to the toe end and having a curved portion and the ground contact portion including the toe end, the sole comprising:
   a bottom surface having an arc shape conforming to an arc shape of the ground contact portion which is convex to a ground contact side, and
   a plurality of recesses and a plurality of protrusions formed on the bottom surface, wherein
   the bottom surface has a curved portion side region adjacent to the curved portion and a toe side region adjacent to the toe end, the curved portion side region and the toe side region being divided by a line extending perpendicular to a direction in which the leaf-spring portion extends, through a contact point where the sole contacts a road surface with the straight portion being aligned with a vertical direction perpendicular to the road surface,
   the toe side region has a constant radius portion adjacent to the toe end and having a constant radius of curvature in a cross-sectional view,
   the curved portion side region has a larger negative ratio than the toe side region, the negative ratio being defined as a ratio of an area of the recesses with respect to a total area of the recesses and the protrusions in a plane view,
   the recesses are provided on the toe side region and form only linear grooves on the constant radius portion of the toe region, and wherein
   in the plane view of the bottom surface,
      the bottom surface includes a zig-zag shaped land portion,
      the zig-zag shaped land portion has a first bent portion bending to be convex to the toe, a second bent portion bending to be convex to the curved portion, and a pair of protruding portions, and
      one of the protruding portions protrudes from the first bent portion of the zig-zag shaped land portion toward the toe end along the bottom surface, and the other of the protruding portions protrudes from the second bent portion of the zig-zag shaped land portion toward the curved portion along the bottom surface.

2. The sole according to claim 1, wherein the curved portion side region includes a first side portion adjacent to the toe side region and a second side portion adjacent to the first side portion with a center of the curved portion side region as a border therebetween, the center of the curved portion side region being a middle point of a maximum length of the curved portion side region measured along the direction in which the leaf-spring portion extends, and
   the first side portion has a larger negative ratio than the second side portion.

3. The sole according to claim 2, wherein the second side region has a larger negative ratio than the toe side region.

4. The sole according to claim 1, wherein the curved portion side region includes a first side portion adjacent to the toe side region and a second side portion adjacent to the first side portion with a center of the curved portion side region as a border therebetween, the center of the curved portion side region being a middle point of a maximum length of the curved portion side region measured along the direction in which the leaf-spring portion extends, and,
   the toe side region includes a first region adjacent to the toe end and a second region adjacent to the curved portion side region, the first region has a constant radius of curvature in a cross-sectional view,
   only the linear grooves are formed by the recesses on the first region in the plane view,
   a length of the first region of the toe side region is smaller than a length of the second region of the toe side region in the direction in which the leaf-spring portion extends, and
   a length of the first side portion of the curved portion side region is larger than the length of the first region of the toe side region in the direction in which the leaf-spring portion extends.

5. The sole according to claim 4, wherein a ratio of a length of the toe side region to a length of the bottom surface in the direction in which the leaf-spring portion extends is 0.25 to 0.8.

6. The sole according to claim 2, wherein
   the toe side region includes a first region adjacent to the toe end and a second region adjacent to the curved portion side region,
   the first region has a constant radius of curvature in a cross-sectional view,
   only the linear grooves are formed by the recesses on the first region in the plane view,
   a length of the first region of the toe side region is smaller than a length of the second region of the toe side region in the direction in which the leaf-spring portion extends, and
   a length of the first side portion of the curved portion side region is larger than the length of the first region of the toe side region in the direction in which the leaf-spring portion extends.

7. The sole according to claim 6, wherein
   each of the first region of the toe side region and first and second side portions of the curved portion side region includes the zig-zag shaped land portion.

8. The sole according to claim 2, wherein the zig-zag shaped land portion includes a portion having the first bent portion and the second bent portion,
   each of the first side portion and the second side portion includes the zig-zag shaped land portion,
   a land portion width of the portion of the zig-zag shaped land portion in the first side portion is larger than a land portion width of the portion of the zig-zag shaped land portion in the second side portion.

9. The sole according to claim 2, wherein the zig-zag shaped land portion includes a portion having the first bent portion and the second bent portion,
   the toe side region includes a first region adjacent to the toe end and a second region adjacent to the curved portion side region, the first region has a constant radius of curvature in a cross-sectional view, each of the first side portion, the second side portion and the second region includes the zig-zag shaped land portion, a land portion width of the portion of the zig-zag shaped land portion in the first side portion is larger than a land portion width of the portion of the zig-zag shaped land portion in the second side portion, a land portion width of the portion of the zig-zag shaped land portion in the second region is larger than the land portion width of the portion of the zig-zag shaped land portion in the first side portion.

10. The sole according to claim 9, wherein only linear grooves are formed by the recesses on the first region in the plane view.

11. The sole according to claim 1, wherein, in the plane view of the bottom surface, the protruding portion has a rounded end.

\* \* \* \* \*